(12) United States Patent
Yan et al.

(10) Patent No.: US 7,008,924 B1
(45) Date of Patent: Mar. 7, 2006

(54) VGF FUSION POLYPEPTIDES

(75) Inventors: Hai Yan, Thousand Oaks, CA (US); Thomas Charles Boone, Newbury Park, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 09/619,198

(22) Filed: Jul. 19, 2000

Related U.S. Application Data

(60) Provisional application No. 60/144,797, filed on Jul. 21, 1999.

(51) Int. Cl.
*C07K 14/575* (2006.01)
*A61K 38/22* (2006.01)

(52) U.S. Cl. .................. 514/12; 530/324; 530/399
(58) Field of Classification Search ............. 530/399, 530/300, 324; 514/12
See application file for complete search history.

(56) References Cited

OTHER PUBLICATIONS

Possenti et al. EMBO J. 8: 2217-2223, 1989.*
Salton J. Neurochem. 57: 991-996, 1991.*
Rudinger, In, "Peptide Hormones" (Ed. J.A. Parsons) University Park Press, Baltimore, pp. 1-7, 1975.*
Canu et al., "Cloning, structural organization analysis, and chromosomal assignment of the human gene for the neurosecretory protein VGF." *Genomics* 15:443-6 (1997).
Schwartz et al., "Hypothalamic response to starvation: implications for the study of wasting disorders." *Am J Physiol* 269:949-57 (1995).
Hahm et al., "Targeted deletion of the Vgf gene indicates that the encoded secretory peptide precursor plays a novel role in the regulation of energy balance." *Neuron* 23:537-48 (1999).
Liu et al., "Peptide V: a VGF-derived neuropeptide purified from bovine posterior pituitary." *Endocrinology* 135:2742-8 (1994).
Trani et al., "Tissue-specific processing of the neuroendocrine protein VGF." *J Neurochem* 65:2441-9 (1995).
Miyatake et al., "The signal transduction pathway for VGF expression due to NGF is different from that due to bFGF in PC12h cell." *Biochem Mol Biol Int* 30:231-6 (1993).
Altshuler and Hirschhorn. "Upsetting the Balance: VGF and the Regulation of Body Weight." *Neuron.* 23:415-417 (1999).

* cited by examiner

*Primary Examiner*—Brenda Brumback
*Assistant Examiner*—Robert C. Hayes
(74) *Attorney, Agent, or Firm*—McDonnell Boehnen Hulbert & Berghoff LLP

(57) ABSTRACT

The present invention provides novel VGF polypeptides and selective binding agents. The invention also provides host cells and methods for producing VGF polypeptides. The invention further provides VGF pharmaceutical compositions and methods for the diagnosis, treatment, amelioration, and/or prevention of diseases, conditions, and disorders associated with VGF polypeptides.

6 Claims, 1 Drawing Sheet

↓ withdrawl of peptide

Peptide 1A - AQEEADAEE - COOH

Dosage: 4 mg/day

Peptide Concentration: 16%

SEQUENCE LISTING

```
<160> NUMBER OF SEQ ID NOS:  10

<210> SEQ ID NO 1
<211> LENGTH: 30
<212> TYPE: PRT
<213> ORGANISM: Rattus norvegicus

<400> SEQUENCE: 1

Ala Gln Glu Glu Ala Asp Ala Glu Glu Arg Arg Leu Gln Glu Gln Glu
  1               5                  10                  15

Glu Leu Glu Asn Tyr Ile Glu His Val Leu Leu His Arg Pro
             20                  25                  30

<210> SEQ ID NO 2
<211> LENGTH: 9
<212> TYPE: PRT
<213> ORGANISM: Rattus norvegicus

<400> SEQUENCE: 2

Ala Gln Glu Glu Ala Asp Ala Glu Glu
  1               5

<210> SEQ ID NO 3
<211> LENGTH: 19
<212> TYPE: PRT
<213> ORGANISM: Rattus norvegicus

<400> SEQUENCE: 3

Leu Gln Glu Gln Glu Glu Leu Glu Asn Tyr Ile Glu His Val Leu Leu
  1               5                  10                  15

His Arg Pro

<210> SEQ ID NO 4
<211> LENGTH: 25
<212> TYPE: PRT
<213> ORGANISM: Rattus norvegicus

<400> SEQUENCE: 4

Leu Glu Gly Ser Phe Leu Gly Gly Ser Glu Ala Gly Glu Arg Leu Leu
  1               5                  10                  15
```

```
Gln Gln Gly Leu Ala Gln Val Glu Ala
         20                  25
```

<210> SEQ ID NO 5
<211> LENGTH: 8
<212> TYPE: PRT
<213> ORGANISM: Rattus norvegicus

<400> SEQUENCE: 5

```
Ser Gln Glu Glu Ala Pro Gly His
 1               5
```

<210> SEQ ID NO 6
<211> LENGTH: 19
<212> TYPE: PRT
<213> ORGANISM: Rattus norvegicus

<400> SEQUENCE: 6

```
His Phe His His Ala Leu Pro Pro Ala Arg His His Pro Asp Leu Glu
 1               5                  10                  15

Ala Gln Ala
```

<210> SEQ ID NO 7
<211> LENGTH: 60
<212> TYPE: PRT
<213> ORGANISM: Rattus norvegicus

<400> SEQUENCE: 7

```
Gln Ala Glu Ala Thr Arg Gln Ala Ala Gln Glu Glu Arg Leu Ala
 1               5                  10                  15

Asp Leu Ala Ser Asp Leu Leu Leu Gln Tyr Leu Leu Gln Gly Gly Ala
             20                  25                  30

Arg Gln Arg Asp Leu Gly Gly Arg Gly Leu Gln Glu Thr Gln Gln Glu
         35                  40                  45

Arg Glu Asn Glu Arg Glu Glu Glu Ala Glu Gln Glu
     50                  55                  60
```

<210> SEQ ID NO 8
<211> LENGTH: 46
<212> TYPE: PRT
<213> ORGANISM: Rattus norvegicus

<400> SEQUENCE: 8

```
Gly Gly Gly Glu Asp Glu Val Gly Glu Glu Asp Glu Glu Ala Ala Glu
 1               5                  10                  15

Ala Glu Ala Glu Ala Glu Glu Ala Glu Arg Ala Arg Gln Asn Ala Leu
             20                  25                  30

Leu Phe Ala Glu Glu Glu Asp Gly Glu Ala Gly Ala Glu Asp
         35                  40                  45
```

<210> SEQ ID NO 9
<211> LENGTH: 49
<212> TYPE: PRT
<213> ORGANISM: Rattus norvegicus

<400> SEQUENCE: 9

```
Asp Ala Glu Gly Thr Glu Glu Gly Gly Glu Asp Asp Asp Glu
 1               5                  10                  15

Glu Met Asp Pro Gln Thr Ile Asp Ser Leu Ile Glu Leu Ser Thr Lys
             20                  25                  30
```

-continued

```
Leu His Leu Pro Ala Asp Asp Val Val Ser Ile Ile Glu Glu Val Glu
            35                  40                  45

Glu

<210> SEQ ID NO 10
<211> LENGTH: 75
<212> TYPE: PRT
<213> ORGANISM: Rattus norvegicus

<400> SEQUENCE: 10

Asn Ala Pro Pro Glu Pro Val Pro Pro Arg Ala Ala Pro Ala Pro
 1               5                  10                  15

Thr His Val Arg Ser Pro Gln Pro Pro Pro Ala Pro Ala Arg Asp
            20                  25                  30

Glu Leu Pro Asp Trp Asn Glu Val Leu Pro Pro Trp Asp Arg Glu Glu
            35                  40                  45

Asp Glu Val Phe Pro Pro Gly Pro Tyr His Pro Phe Pro Asn Tyr Ile
        50                  55                  60

Arg Pro Arg Thr Leu Gln Pro Pro Ala Ser Ser
65                  70                  75
```

VGF FUSION POLYPEPTIDES

This application claims the benefit of priority to U.S. Provisional Patent Application No. 60/144,797, filed on Jul. 21, 1999, the disclosure of which is explicitly incorporated by reference herein.

FIELD OF THE INVENTION

This invention relates to novel VGF polypeptides and selective binding agents. The invention also relates to host cells and methods for producing VGF polypeptides. The invention further relates to VGF pharmaceutical compositions and methods for the diagnosis, treatment, amelioration, and/or prevention of diseases, conditions, and disorders associated with VGF polypeptides.

BACKGROUND OF THE INVENTION

VGF is a secreted polypeptide that is found in neurons and endocrine cells. Canu et al., 1997, *Genomics*, 45:443–46. VGF is found in the hypothalamus, and is regulated in the brain by electrical activity, injury, and the circadian clock. The hypothalamus has been shown to play an important role in the regulation of food intake and energy output, and damage to the hypothalamus has been shown to effect both appetite and body weight. Schwartz et al., 1995, *Am. J. Physiol.*, 269:949–57. VGF also has been found to play a role in metabolism.

The nucleotide and amino acid sequences of human and rat VGF are known, and show a high homology to one another. Canu et al., supra. The VGF gene, which was originally identified as a 2.7 kb cDNA fragment, is transcribed in subpopulations of neurons and endocrine cells in vitro by neurotrophins.

Obesity and anorexia are disruptions of energy homeostasis, resulting from imbalances between energy intake and expenditure. There is a need for effective treatment of these conditions. There is also a need for effective treatment of cachexia, sterility, hypermetabolic conditions, hyperactivity, hypoactivity, hyperinsulin production, and related conditions and disorders.

SUMMARY OF THE INVENTION

The present invention provides for an isolated polypeptide comprising the amino acid sequence as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. A preferred isolated polypeptide comprises the amino acid sequence as set forth in SEQ ID NO: 2.

The invention also provides for an isolated polypeptide comprising a fragment of the amino acid sequence as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10 wherein the fragment has an activity of the polypeptide as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. A preferred isolated polypeptide comprises a fragment of the amino acid sequence as set forth in SEQ ID NO: 2 wherein the fragment has an activity of the polypeptide as set forth in SEQ ID NO: 2.

The invention further provides for an isolated polypeptide comprising the amino acid sequence selected from the group consisting of:

(a) the amino acid sequence as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10 with at least one conservative amino acid substitution and wherein the polypeptide has an activity of the polypeptide as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10;

(b) the amino acid sequence as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10 with at least one amino acid insertion and wherein the polypeptide has an activity of the polypeptide as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10;

(c) the amino acid sequence as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10 with at least one amino acid deletion and wherein the polypeptide has an activity of the polypeptide as set forth in any of SEQ ID NO: 1, SEQ ID NO:2, SEQ ID NO:3, SEQ ID NO:4, SEQ ID NO: 5, SEQ ID NO: 6, SEQ ID NO: 7, SEQ ID NO: 8, SEQ ID NO: 9, or SEQ ID NO: 10;

(d) the amino acid sequence as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10 which has a C- and/or N-terminal truncation and wherein the polypeptide has an activity of the polypeptide as set forth in wherein the polypeptide has an activity of the polypeptide as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; and (e) the amino acid sequence as set forth in any of SEQ ID NO: 1, SEQ ID NO:2, SEQ ID NO:3, SEQ ID NO:4, SEQ ID NO: 5, SEQ ID NO: 6, SEQ ID NO: 7, SEQ ID NO: 8, SEQ ID NO: 9, or SEQ ID NO: 10 with at least one modification selected from the group consisting of amino acid substitutions, amino acid insertions, amino acid deletions, carboxyl-terminal truncation, and amino-terminal truncation and wherein the polypeptide has an activity of the polypeptide as set forth in any of SEQ ID NO: 1, SEQ ID NO:2, SEQ ID NO:3, SEQ ID NO:4, SEQ ID NO:5, SEQ ID NO: 6, SEQ ID NO: 7, SEQ ID NO: 8, SEQ ID NO: 9, or SEQ ID NO: 10.

Also provided are fusion polypeptides comprising at least one polypeptide as described fused to a heterologous amino acid sequence.

The present invention also provides selective binding agents, such as antibodies, capable of specifically binding at least one polypeptide comprising the amino acid sequence as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

The present invention further provides selective binding agents capable of specifically binding a fragment of at least one polypeptide comprising the amino acid sequence as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10, or a naturally occurring variant thereof.

The selective binding agents of the present invention can be antibodies, or fragments thereof, including, but not limited to: murine antibodies, humanized antibodies, human antibodies, polyclonal antibodies, monoclonal antibodies, chimeric antibodies, CDR-grafted antibodies, antiidiotypic antibodies, and variable region fragments (such as Fab or a Fab' fragments). The selective binding agents of the present invention include selective binding agents or fragments thereof having at least one complementarity-determining region with specificity for a polypeptide comprising the amino acid sequence as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

The selective binding agents of the invention can optionally be bound to a detectable label.

Also provided are selective binding agents that are capable of antagonizing VGF biological activity.

A preferred selective binding agent, or fragment thereof, is capable of specifically binding a polypeptide comprising the amino acid sequence as set forth in SEQ ID NO: 2, or a fragment thereof.

The present invention also provides pharmaceutical compositions comprising the polypeptides or selective binding agents of the invention and one or more pharmaceutically acceptable formulation agents are also encompassed by the invention. The formulation agent can be a suitable carrier, adjuvant, solubilizer, stabilizer, or anti-oxidant. VGF polypeptides or selective binding agents can be covalently modified with a water-soluble polymer, such as polyethylene glycol and dextran. The pharmaceutical compositions of the present invention are used to provide therapeutically effective amounts of the VGF polypeptides or selective binding agents of the present invention. The present invention also provides methods for the manufacture of a medicament for the treatment of VGF-related diseases, conditions, or disorders.

The present invention further provides methods for treating, preventing, or ameliorating a VGF-related disease, condition, or disorder comprising administering to a patient an effective amount of the VGF polypeptides or selective binding agents of the invention. VGF-related diseases, conditions, and disorders include obesity, sterility, cachexia, eating disorders, AIDS-related complex, hypermetabolic conditions, hyperactivity, hypoactivity, and hyperinsulin production. VGF-related eating disorders include bulimia and anorexia nervosa. It will be appreciated that the methods of the present invention also provide for the administration of combinations of the VGF polypeptides or selective binding agents of the present invention.

Also provided are methods of diagnosing a VGF-related disease, condition, or disorder, or a susceptibility to a VGF-related disease, condition, or disorder, in an animal comprising determining the presence or amount of expression of a VGF polypeptide and diagnosing the VGF-related disease, condition, or disorder, or susceptibility to a VGF-related disease, condition, or disorder, based on the presence or amount of expression of the VGF polypeptide. In preferred methods of diagnosing a VGF-related disease, condition, or disorder, or a susceptibility to a VGF-related disease, condition, or disorder, the animal is a mammal. In even more preferred methods the animal is a human.

The present invention also provides a method of assaying test molecules to identify a test molecule that binds to a VGF polypeptide. The method comprises contacting a VGF polypeptide with a test molecule and determining the extent of binding of the test molecule to the polypeptide. The method further comprises determining whether such test molecules are agonists or antagonists of a VGF polypeptide. The present invention further provides a method of testing the impact of molecules on the expression of VGF polypeptide or on the activity of VGF polypeptide.

These and other objects of the invention will become evident upon consideration of the specification as a whole.

BRIEF DESCRIPTION OF THE FIGURES

FIG. 2 illustrates the antibody titer levels of a rabbit injected with VGF-1 (SEQ ID NO:1), calculated at 1:100 to 2× serial dilution;

FIG. 3 illustrates the antibody titer levels of a rabbit injected with VGF-2 (SEQ ID NO:4), calculated at 1:100 to 2× serial dilution.

DETAILED DESCRIPTION OF THE INVENTION

Figure 1:
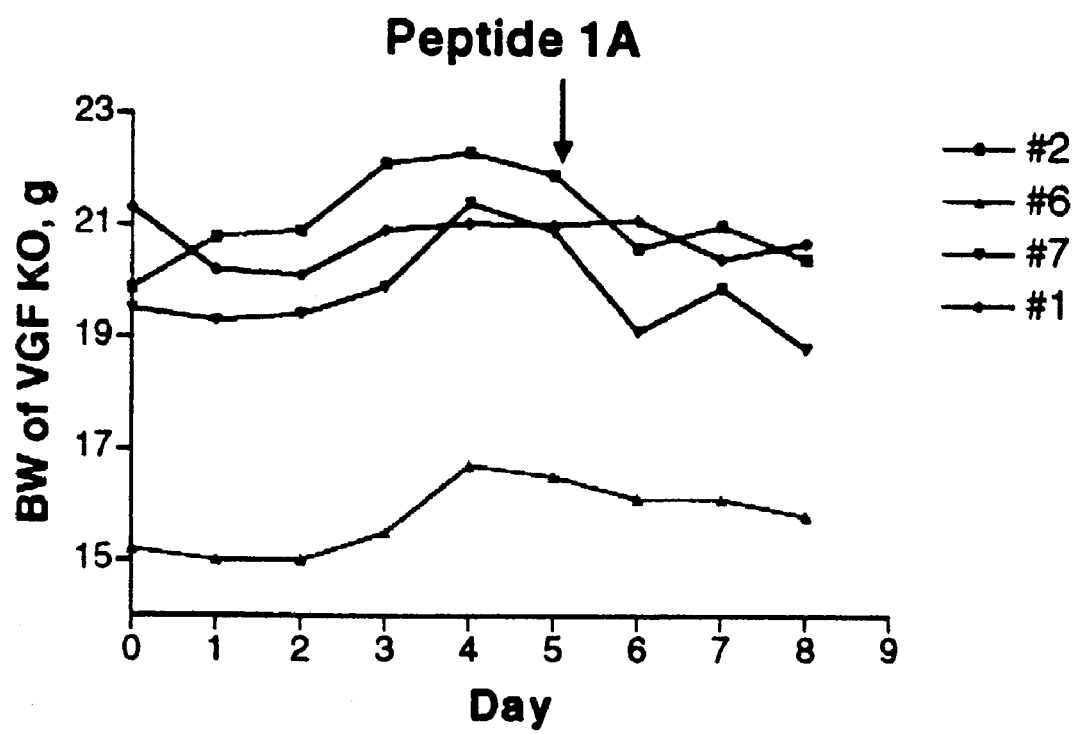
FIG. 1 illustrates the body weight of VGF knockout mice (#2, #6, #7, and #1) following administration of VGF-1a (SEQ ID NO: 2). The administration of VGF-1a was ceased at day 5 (as indicated by the arrow)

The section headings used herein are for organizational purposes only and are not to be construed as limiting the subject matter described. All references cited in this application are expressly incorporated by reference herein.

Definitions

The term "VGF polypeptide" refers to a polypeptide comprising any of the amino acid sequences as set forth in Table I, and related polypeptides described herein. Related polypeptides include VGF polypeptide fragments, orthologs, variants, and derivatives, which possess at least one characteristic of any of the VGF polypeptides set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. The term "VGF polypeptide fragments" also refers to amino-terminal and/or carboxyl-terminal truncations of VGF polypeptide orthologs, variants, or derivatives. VGF polypeptide fragments may result from alternative RNA splicing or from in vivo protease activity. Such VGF polypeptide fragments may optionally comprise an amino-terminal methionine residue. It will be appreciated that such fragments can be used, for example, to generate antibodies to VGF polypeptides.

The term "VGF polypeptide ortholog" refers to a polypeptide from another species that corresponds to any of the VGF polypeptides as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. For example, mouse and human VGF polypeptides are considered orthologs of each other.

The term "VGF polypeptide variants" refers to VGF polypeptides comprising amino acid sequences having one or more amino acid sequence substitutions (conservative, non-conservative, or combination thereof), deletions (such as internal deletions and/or VGF polypeptide fragments), and/or additions (such as internal additions and/or VGF fusion polypeptides) as compared to any of the VGF polypeptides as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. Variants may be naturally occurring (e.g., VGF polypeptide allelic variants or VGF polypeptide orthologs) or artificially constructed.

The term "VGF polypeptide derivatives" refers to any of the VGF polypeptides as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10, or VGF polypeptide fragments, orthologs, or variants, as defined herein, that have been chemically modified. Chemical modifications, may be, for example, by covalent attachment of one or more polymers, including, but limited to, water-soluble polymers, N-linked or O-linked carbohydrates, sugars, and 4, SEQ ID NO: 5, SEQ ID NO: 6, SEQ ID NO: 7, SEQ ID NO: 8, SEQ ID NO: 9, or SEQ ID NO: 10. VGF polypeptides may be mature polypeptides, as defined herein, and may or may not have an amino-terminal methionine residue, depending on the method by which they are prepared.

10. In addition, a VGF polypeptide may be active as an immunogen; that is, the VGF polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

TABLE I

VGF Polypeptides

| VGF Polypeptide | Amino Acid Sequence | (SEQ ID) |
|---|---|---|
| VGF-1 | AQEEADAEERRLQEQEELENYIEHVLLHRP | (SEQ ID NO: 1) |
| VGF-1a | AQEEADAEE | (SEQ ID NO: 2) |
| VGF-1b | LQEQEELENYIEHVLLHRP | (SEQ ID NO: 3) |
| VGF-2 | LEGSFLGGSEAGERLLQQGLAQVEA | (SEQ ID NO: 4) |
| VGF-3 | SQEEAPGH | (SEQ ID NO: 5) |
| VGF-4 | HFHHALPPARHHPDLEAQA | (SEQ ID NO: 6) |
| VGF-5 | QAEATRQAAAQEERLADLASDLLLQYLLQGGARQRDLGGRGLQE TQQERENEREEEAEQE | (SEQ ID NO: 7) |
| VGF-6 | GGGEDEVGEEDEEAAEAEAEAEEAERARQNALLFAEEEDGEAGA ED | (SEQ ID NO: 8) |
| VGF-7 | DAEGTEEGGEEDDDDEEMDPQTIDSLIELSTKLHLPADDVVSII EEVEE | (SEQ ID NO: 9) |
| VGF-8 | NAPPEPVPPPRAAPAPTHVRSPQPPPPAPARDELPDWNEVLPPW DREEDEVFPPGPYHPFPNYIRPRTLQPPASS | (SEQ ID NO: 10) |

The term "VGF polypeptide fragment" refers to a polypeptide that comprises a truncation at the amino-terminus and/or a truncation at the carboxyl-terminus of any of the VGF polypeptides set forth in SEQ ID NO: 1, SEQ ID NO: 2, SEQ ID NO: 3, phosphates. VGF polypeptide derivatives are modified in a manner that is different from naturally occurring VGF polypeptide, either in the type or location of the molecules attached to the polypeptide. VGF polypeptide derivatives further include VGF polypeptides having a deletion of one or more chemical groups naturally attached to the VGF polypeptide.

The term "mature VGF polypeptide" refers to a VGF polypeptide lacking a leader sequence. A mature VGF polypeptide may also include other modifications such as proteolytic processing of the amino-terminus (with or without a leader sequence) and/or the carboxyl-terminus, cleavage of a smaller polypeptide from a larger precursor, N-linked and/or O-linked glycosylation, and the like.

The term "VGF fusion polypeptide" refers to a fusion of one or more amino acids (such as a heterologous peptide or polypeptide) at the amino or carboxyl-terminus of a VGF polypeptide, fragment, ortholog, variant, or derivative.

The term "biologically active VGF polypeptides" refers to VGF polypeptides having at least one activity characteristic of the polypeptide comprising the amino acid sequence as set forth in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO:

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "identity," as known in the art, refers to a relationship between the sequences of two or more polypeptide molecules or two or more nucleic acid molecules, as determined by comparing the sequences. In the art, "identity" also means the degree of sequence relatedness between polypeptides or nucleic acid molecules, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The terms "effective amount" and "therapeutically effective amount" each refer to the amount of a VGF polypeptide used to support an observable level of one or more biological activities of the VGF polypeptides as set forth herein.

The term "pharmaceutically acceptable carrier" or "physiologically acceptable carrier" as used herein refers to one or more formulation materials suitable for accomplishing or enhancing the delivery of the VGF polypeptide or VGF selective binding agent as a pharmaceutical composition.

The term "selective binding agent" refers to a molecule or molecules having specificity for a VGF polypeptide. As used herein, the terms, "specific" and "specificity" refer to the ability of the selective binding agents to bind to VGF polypeptides and not to bind to non-VGF polypeptides. It will be appreciated, however, that the selective binding agents may also bind VGF orthologs.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Relatedness of VGF Polypeptides

Conservative modifications to the amino acid sequence of a VGF polypeptide will produce a polypeptide having functional and chemical characteristics similar to those of the VGF polypeptide. In contrast, substantial modifications in the functional and/or chemical characteristics of VGF polypeptides may be accomplished by selecting substitutions in the amino acid sequence of the VGF polypeptide that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of a VGF polypeptide that are homologous with other VGF polypeptide orthologs, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105–31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within +2 is preferred, those which are within +1 are particularly preferred, and those within +0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the VGF polypeptide, or to increase or decrease the affinity of the VGF polypeptides described herein.

Exemplary amino acid substitutions are set forth in Table II.

TABLE II

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable VGF polypeptide variants using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of a VGF polypeptide to such similar polypeptides. With such a comparison, one can identify residues and portions of the molecules that are conserved among similar polypeptides. It will be appreciated that changes in areas of the VGF molecule that are not conserved relative to such similar polypeptides would be less likely to adversely affect the biological activity and/or structure of a VGF polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a VGF polypeptide that correspond to amino acid residues that are important for activity or structure in similar polypeptides. One skilled in the art may opt for chemically similar amino acid substitutions for such predicted important amino acid residues of VGF polypeptides.

One skilled in the art can also analyze the three-dimensional structure and amino acid sequence in relation to that structure in similar polypeptides. In view of such information, one skilled in the art may predict the alignment of amino acid residues of VGF polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Opin. Biotechnol.* 7:422–27; Chou et al., 1974, *Biochemistry* 13:222–45; Chou et al., 1974, *Biochemistry* 113:211–22; Chou et al., 1978, *Adv. Enzymol. Relat. Areas Mol. Biol.* 47:45–48; Chou et al., 1978, *Ann. Rev. Biochem.* 47:251–276; and Chou et al., 1979, *Biophys. J.* 26:367–84. Moreover, computer programs are currently available to assist with predicting secondary structure. One method of predicting secondary structure is based upon homology modeling. For example, two polypeptides or proteins that have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999, *Nucleic Acids Res.* 27:244–47. It has been suggested that there are a limited number of folds in a given polypeptide or protein and that once a critical number of structures have been resolved, structural prediction will become dramatically more accurate (Brenner et al., 1997, *Curr. Opin. Struct. Biol.* 7:369–76).

Additional methods of predicting secondary structure include "threading" (Jones, 1997, *Curr. Opin. Struct. Biol.* 7:377–87; Sippl et al., 1996, *Structure* 4:15– 19), "profile analysis" (Bowie et al., 1991, *Science,* 253:164–70; Gribskov et al., 1990, *Methods Enzymol.* 183:146–59; Gribskov et al., 1987, *Proc. Nat. Acad. Sci.* U.S.A. 84:4355–58), and "evolutionary linkage" (See Holm et al., supra, and Brenner et al., supra).

Preferred VGF polypeptide variants include glycosylation variants wherein the number and/or type of glycosylation sites have been altered compared to the amino acid sequence of the VGF polypeptides of the present invention. In one embodiment, VGF polypeptide variants comprise a greater or a lesser number of N-linked glycosylation sites than the amino acid sequence of the VGF polypeptides of the present invention. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred VGF variants include cysteine variants, wherein one or more cysteine residues are deleted or substituted with another amino acid (e.g., serine) as compared to the amino acid sequence of the VGF polypeptides of the present invention. Cysteine variants are useful when VGF polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In addition, VGF polypeptides may be fused to a homologous polypeptide to form a homodimer or to a heterologous polypeptide to form a heterodimer. Heterologous peptides and polypeptides include, but are not limited to: an epitope to allow for the detection and/or isolation of a VGF fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the VGF polypeptides of the present invention.

Fusions can be made either at the amino-terminus or at the carboxyl-terminus of a VGF polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, a VGF polypeptide is fused to one or more domains of an Fc region of human IgG. Antibodies comprise two functionally independent parts, a variable domain known as "Fab," that binds antigen, and a constant domain known as "Fc," that is involved in effector functions such as complement activation and attack by phagocytic cells. An Fc has a long serum half-life, whereas an Fab is short-lived. Capon et al., 1989, *Nature* 337:525–31. When constructed together with a therapeutic protein, an Fc domain can provide longer half-life or incorporate such functions as Fc receptor binding, protein A binding, complement fixation, and perhaps even placental transfer. Id. Table III summarizes the use of certain Fc fusions known in the art.

TABLE III

Fc Fusion with Therapeutic Proteins

| Form of Fc | Fusion partner | Therapeutic implications | Reference |
| --- | --- | --- | --- |
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., 1995, J. Immunol. 154: 5590–600 |
| IgG1 | TNF receptor | septic shock | Fisher et al., 1996, N. Engl. J. Med. 334: 1697–1702; Van Zee et al., 1996, J. |

TABLE III-continued

Fc Fusion with Therapeutic Proteins

| Form of Fc | Fusion partner | Therapeutic implications | Reference |
|---|---|---|---|
| IgG, IgA, IgM, or IgE (excluding the first domain) | TNF receptor | inflammation, autoimmune disorders | Immunol. 156: 2221–30 U.S. Pat. No. 5,808,209 |
| IgG1 | CD4 receptor | AIDS | Capon et al., 1989, Nature 337:525–31 |
| IgG1, IgG3 | N-terminus of IL-2 | anti-cancer, antiviral | Harvill et al., 1995, Immunotech, 1:95–105 |
| IgG1 | C-terminus of OPG | osteoarthritis; bone density | WO 97/23614 |
| IgG1 | N-terminus of leptin | anti-obesity | PCT/US 97/23183, filed Dec. 11, 1997 |
| Human Ig Cγ1 | CTLA-4 | autoimmune disorders | Linsley, 1991, J. Exp. Med., 174: 561–69 |

In one example, a human IgG hinge, CH2, and CH3 region may be fused at either the amino-terminus or carboxyl-terminus of the VGF polypeptides using methods known to the skilled artisan. The resulting VGF fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, or reduced aggregation.

Identity and similarity of related polypeptides can be readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heinle, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J. Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, and FASTA (Altschul et al., 1990, *J. Mol. Biol.* 215:403–10). The BLASTX program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978) (PAM250 comparison matrix); Henikoff et al., 1992, *Proc. Natl. Acad. Sci* USA 89:10915–19 (BLOSUM 62 comparison matrix)).

Preferred parameters for polypeptide sequence comparison include the following:

Algorithm: Needleman and Wunsch, 1970, *J. Mol. Biol.* 48:443–53;
Comparison matrix: BLOSUM 62 (Henikoff et al., supra);
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of a VGF polypeptide can readily be obtained in a variety of ways including, without limitation, chemical synthesis, cDNA or genomic library screening, expression library screening, and/or PCR amplification of cDNA.

Recombinant DNA methods used herein are generally those set forth in Sambrook et al., *Molecular Cloning: A Laboratory Manual* (Cold Spring Harbor Laboratory Press, 1989) and *Current Protocols in Molecular Biology* (Ausubel et al., eds., Green Publishers Inc. and Wiley and Sons 1994).

Nucleic acid molecules encoding the amino acid sequence of VGF polypeptides may be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes the amino acid sequence of a VGF polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a VGF polypeptide can be inserted into an expression vector. By introducing the expression vector into an appropriate host, the encoded VGF polypeptide may be produced in large amounts.

Another method for obtaining a suitable nucleic acid sequence is the polymerase chain reaction (PCR). In this method, cDNA is prepared from poly(A)+ RNA or total RNA using the enzyme reverse transcriptase. Two primers, typically complementary to two separate regions of cDNA encoding the amino acid sequence of a VGF polypeptide, are then added to the cDNA along with a polymerase such as Taq polymerase, and the polymerase amplifies the cDNA region between the two primers.

Another means of preparing a nucleic acid molecule encoding the amino acid sequence of a VGF polypeptide is chemical synthesis using methods well known to the skilled artisan such as those described by Engels et al., 1989, *Angew. Chem. Intl. Ed.* 28:716–34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a VGF polypeptide will be several hundred nucleotides in length. Nucleic acids larger than about 100 nucleotides can be synthesized as several fragments using these methods. The fragments can then be ligated together to form the full-length nucleotide sequence of a VGF gene. Usually, the DNA fragment encoding the amino-terminus of the polypeptide will have an ATG, which encodes a methionine residue. This methionine may or may not be present on the mature form of the VGF polypeptide, depending on whether the polypeptide produced in the host cell is designed to be secreted from that cell. Other methods known to the skilled artisan may be used as well.

In certain embodiments, nucleic acid variants contain codons which have been altered for optimal expression of a VGF polypeptide in a given host cell. Particular codon alterations will depend upon the VGF polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "Drosophila_high.cod," "Human_high.cod," "Maize_high.cod," and "Yeast_high.cod."

In some cases, it may be desirable to prepare nucleic acid molecules encoding VGF polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Vectors and Host Cells

A nucleic acid molecule encoding the amino acid sequence of a VGF polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a VGF polypeptide may be amplified/expressed in prokaryotic, yeast, insect (baculovirus systems) and/or eukaryotic host cells. Selection of the host cell will depend in part on whether a VGF polypeptide is to be post-translationally modified (e.g., glycosylated and/or phosphorylated). If so, yeast, insect, or mammalian host cells are preferable. For a review of expression vectors, see *Meth. Enz.*, vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the Vector may contain a "tag"-encoding sequence, i.e., an oligonucleotide molecule located at the 5' or 3' end of the VGF polypeptide coding sequence; the oligonucleotide sequence encodes polyHis (such as hexa-His), or another "tag" such as FLAG, HA (hemaglutinin influenza virus), or myc for which commercially available antibodies exist. This tag is typically fused to the polypeptide upon expression of the polypeptide, and can serve as a means for affinity purification of the VGF polypeptide from the host cell. Affinity purification can be accomplished, for example, by column chromatography using antibodies against the tag as an affinity matrix. Optionally, the tag can subsequently be removed from the purified VGF polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate VGF polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

Useful flanking sequences may be obtained by any of several methods well known in the art. Typically, flanking sequences useful herein—other than the VGF gene flanking sequences—will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of a VGF polypeptide. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a VGF polypeptide. As a result, increased quantities of VGF polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a VGF polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a VGF polypeptide out of the host cell. Typically, a nucleotide sequence encoding the signal sequence is positioned in the coding region of a VGF nucleic acid molecule, or directly at the 5'end of a VGF polypeptide coding region. Many signal sequences have been identified, and any of those that are functional in the selected host cell may be used in conjunction with a VGF nucleic acid molecule. Therefore, a signal sequence may be homologous (naturally occurring) or heterologous to the VGF nucleic acid molecule. Additionally, a signal sequence may be chemically synthesized using methods described herein. In most cases, the secretion of a VGF polypeptide from the host cell via the presence of a signal peptide will result in the removal of the signal peptide from the secreted VGF polypeptide. The signal sequence may be a component of the vector, or it may be a part of a VGF nucleic acid molecule that is inserted into the vector.

A nucleotide sequence encoding a native VGF polypeptide signal sequence may be joined to a VGF polypeptide coding region or a nucleotide sequence encoding a heterologous signal sequence may be joined to a VGF polypeptide coding region. The heterologous signal sequence selected should be one that is recognized and processed, i.e., cleaved by a signal peptidase, by the host cell. For prokaryotic host cells that do not recognize and process the native VGF polypeptide signal sequence, the signal sequence is substituted by a prokaryotic signal sequence selected, for example, from the group of the alkaline phosphatase, penicillinase, or heat-stable enterotoxin II leaders. For yeast secretion, the native VGF polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired VGF polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the VGF gene especially where the gene used is a full-length genomic sequence or a fragment thereof. Where the intron is not naturally occurring within the gene (as for most cDNAs), the intron may be obtained from another source. The position of the intron with respect to flanking sequences and the VGF gene is generally important, as the intron must be transcribed to be effective. Thus, when a VGF cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used, provided that it is compatible with the host cell into which it is inserted. Also included herein are synthetic introns. Optionally, more than one intron may be used in the vector.

Expression and cloning vectors will typically contain a promoter that is recognized by the host organism and operably linked to the molecule encoding the VGF polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding VGF polypeptide by removing the promoter from the source DNA by restriction enzyme digestion and inserting the desired promoter sequence into the vector. The native VGF promoter sequence may be used to direct amplification and/or expression of a VGF nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling VGF gene expression include, but are not limited to: the SV40 early promoter region (Bernoist and Chambon, 1981, *Nature* 290:304–10); the CMV promoter; the promoter contained in the 3' long terminal repeat of Rous sarcoma virus (Yamamoto, et al., 1980, *Cell* 22:787–97); the herpes thymidine kinase promoter (Wagner et al., 1981, *Proc. Natl. Acad. Sci. U.S.A.* 78:1444–45); the regulatory sequences of the metallothionine gene (Brinster et al., 1982, *Nature* 296:39–42); prokaryotic expression vectors such as the beta-lactamase promoter (Villa-Kamaroff et al., 1978, *Proc. Natl. Acad. Sci. U.S.A.*, 75:3727–31); or the tac promoter (DeBoer et al., 1983, *Proc. Natl. Acad. Sci. U.S.A.*, 80:21–25). Also of interest are the following animal transcriptional control regions, which exhibit tissue specificity and have been utilized in transgenic animals: the elastase I gene control region which is active in pancreatic acinar cells (Swift et al., 1984, *Cell* 38:639–46; Omitz et al., 1986, *Cold Spring Harbor Symp. Quant. Biol.* 50:399–409 (1986); MacDonald, 1987, *Hepatology* 7:425–515); the insulin gene control region which is active in pancreatic beta cells (Hanahan, 1985, *Nature* 315:115–22); the immunoglobulin gene control region which is active in lymphoid cells (Grosschedl et al., 1984, *Cell* 38:647–58; Adames et al., 1985, *Nature* 318:533–38; Alexander et al., 1987, *Mol. Cell. Biol.*, 7:1436–44); the mouse mammary tumor virus control region which is active in testicular, breast, lymphoid and mast cells (Leder et al., 1986, *Cell* 45:485–95); the albumin gene control region which is active in liver (Pinkert et al., 1987, *Genes and Devel.* 1:268–76); the alpha-feto-protein gene control region which is active in liver (Krumlauf et al., 1985, *Mol. Cell. Biol.*, 5:1639–48; Hammer et al., 1987, *Science* 235:53–58); the alpha 1-antitrypsin gene control region which is active in the liver (Kelsey et al., 1987, *Genes and Devel.* 1:161–71); the beta-globin gene control region which is active in myeloid cells (Mogram et al., 1985, *Nature* 315:338–40; Kollias et al., 1986, *Cell* 46:89–94); the myelin basic protein gene control region which is active in oligodendrocyte cells in the brain (Readhead et al., 1987, *Cell* 48:703–12); the myosin light chain-2 gene control region which is active in skeletal muscle (Sani, 1985, *Nature* 314:283–86); and the gonadotropic releasing hormone gene control region which is active in the hypothalamus (Mason et al., 1986, *Science* 234:1372–78).

An enhancer sequence may be inserted into the vector to increase the transcription in higher eukaryotes of a DNA encoding a VGF polypeptide. Enhancers are cis-acting elements of DNA, usually about 10–300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a VGF nucleic acid molecule, it is typically located at a site 5' from the promoter.

Expression vectors may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors are those which are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Pub. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems, La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.).

After the vector has been constructed and a nucleic acid molecule encoding a VGF polypeptide has been inserted into the proper site of the vector, the completed vector may be inserted into a suitable host cell for amplification and/or polypeptide expression. The transformation of an expression vector for a VGF polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cell). The host cell, when cultured under appropriate conditions, synthesizes a VGF polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(−) cells (Urlaub et al., 1980, *Proc. Natl. Acad. Sci. U.S.A.* 97:4216–20), human embryonic kidney (HEK) 293 or 293T cells, or 3T3 cells.

The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as suitable host cells are bacterial cells. For example, the various strains of *E. coli* (e.g., HB101, DH5α, DH10, and MC1061) are well known as host cells in the field of biotechnology. Various strains of *B. subtilis*, *Pseudomonas* spp., other *Bacillus* spp., *Streptomyces* spp., and the like may also be employed in this method.

Many strains of yeast cells known to those skilled in the art are also available as host cells for the expression of VGF polypeptides. Preferred yeast cells include, for example, *Saccharomyces cerivisae* and *Pichia pastoris*.

Additionally, where desired, insect cell systems may be utilized for the expression of VGF polypeptides. Such systems are described, for example, in Kitts et al., 1993, *Biotechniques*, 14:810–17; Lucklow, 1993, *Curr. Opin. Biotechnol.* 4:564–72; and Lucklow et al., 1993, *J. Virol.*, 67:4566–79. Preferred insect cells are Sf-9 and Hi5 (Invitrogen).

One may also use transgenic animals to express glycosylated VGF polypeptides. For example, one may use a transgenic milk-producing animal (a cow or goat, for example) and obtain the present glycosylated polypeptide in the animal milk. One may also use plants to produce VGF polypeptides, however, in general, the glycosylation occurring in plants is different from that produced in mammalian cells, and may result in a glycosylated product which is not suitable for human therapeutic use.

Polypeptide Production

Host cells comprising a VGF polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a VGF polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a VGF polypeptide has been designed to be secreted from the host cells, the majority of polypeptide may be found in the cell culture medium. If however, the VGF polypeptide is not secreted from the host cells, it will be present in the cytoplasm and/or the nucleus (for eukaryotic host cells) or in the cytosol (for gram-negative bacteria host cells).

For a VGF polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a VGF polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized VGF polypeptide can then be analyzed using gel electrophoresis, immunoprecipitation, or the like. If it is desired to isolate the VGF polypeptide, isolation may be accomplished using standard methods such as those described herein and in Marston et al., 1990, *Meth. Enz.*, 182:264–75.

In some cases, a VGF polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol(DTT)/ dithiane DTT, and 2-2-mercaptoethanol(bME)/dithio-b (ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of a VGF polypeptide, then the polypeptide will be found primarily in the supernatant after centrifugation of the cell homogenate. The polypeptide may be further isolated from the supernatant using methods such as those described herein.

The purification of a VGF polypeptide from solution can be accomplished using a variety of techniques. If the polypeptide has been synthesized such that it contains a tag such as Hexahistidine (VGF polypeptide/hexaHis) or other small peptide such as FLAG (Eastman Kodak Co., New Haven, Conn.) or myc (Invitrogen, Carlsbad, Calif.) at either its carboxyl or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification of VGF polypeptide/polyHis. See, e.g., *Current Protocols in Molecular Biology* § 10.11.8 (Ausubel et al., eds., Green Publishers Inc. and Wiley and Sons 1993).

Additionally, VGF polypeptides may be purified through the use of a monoclonal antibody that is capable of specifically recognizing and binding to a VGF polypeptide.

In situations where it is preferable to partially or completely purify a VGF polypeptide such that it is partially or substantially free of contaminants, standard methods known to those skilled in the art may be used. Such methods include, without limitation, separation by electrophoresis followed by electroelution, various types of chromatography (affinity, immunoaffinity, molecular sieve, and ion exchange), HPLC, and preparative isoelectric focusing ("Isoprime" machine/technique, Hoefer Scientific, San Francisco, Calif.). In some cases, two or more purification techniques may be combined to achieve increased purity.

VGF polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. USA* 82:5132; and Stewart and Young, Solid Phase Peptide Synthesis (Pierce Chemical Co. 1984). Such polypeptides may be synthesized with or without a methionine on the amino-terminus. Chemically synthesized VGF polypeptides may be oxidized using methods set forth in these references to form disulfide bridges. Chemically synthesized VGF polypeptides are expected to have comparable biological activity to the corresponding VGF polypeptides produced recombinantly or purified from natural sources, and thus may be used interchangeably with a recombinant or natural VGF polypeptide.

Another means of obtaining VGF polypeptide is via purification from biological samples such as source tissues and/or fluids in which the VGF polypeptide is naturally found. Such purification can be conducted using methods for protein purification as described herein. The presence of the VGF polypeptide during purification may be monitored, for example, using an antibody prepared against recombinantly produced VGF polypeptide or peptide fragments thereof.

A number of additional methods for producing polypeptides are known in the art, and the methods can be used to produce polypeptides having specificity for VGF polypeptide. See, e.g., Roberts et al., 1997, *Proc. Natl. Acad. Sci. U.S.A.* 94:12297–303, which describes the production of fusion proteins between an mRNA and its encoded peptide. See also, Roberts, 1999, *Curr. Opin. Chem. Biol.* 3:268–73.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive IL-17 like protein expression libraries, which can subsequently be used for high throughput phenotypic screening in a variety of assays, such as biochemical assays, cellular assays, and whole organism assays (e.g., plant, mouse, etc.).

Synthesis

It will be appreciated by those skilled in the art that the VGF polypeptide molecules described herein may be produced by recombinant and other means.

Selective Binding Agents

The term "selective binding agent" refers to a molecule that has specificity for one or more VGF polypeptides. Suitable selective binding agents include, but are not limited to, antibodies and derivatives thereof, polypeptides, and small molecules. Suitable selective binding agents are prepared using methods known in the art. An exemplary VGF polypeptide selective binding agent of the present invention is capable of binding a certain portion of the VGF polypeptide thereby inhibiting the binding of the polypeptide to a VGF polypeptide receptor.

The term "antigen" refers to a molecule or a portion of a molecule capable of being bound by a selective binding agent and additionally capable of being used in an animal to produce antibodies capable of binding to an epitope of that antigen. An antigen may have one or more epitopes.

The term "epitope" refers to that portion of any molecule capable of being recognized by and bound by a selective binding agent at one or more antigen-binding regions of the binding agent. Epitopes usually consist of chemically active surface groupings of molecules such as amino acids or sugar side chains having specific three-dimensional structural characteristics as well as specific charge characteristics. The terms "inhibiting epitope" and "neutralizing epitope" refer to an epitope which, when bound by a selective binding agent, results in a loss of biological activity of the molecule containing the epitope, in vivo, in vitro, or in situ, more preferably in vivo, including binding of VGF polypeptides to a VGF polypeptide receptor.

As used herein, the term "antigen-binding region" refers to that portion of the selective binding agent which contains the amino acid residues that interact with an antigen and confer on the binding agent its specificity and affinity for the antigen. Preferably, the antigen-binding region will be of murine origin. In other embodiments, the antigen-binding region can be derived from other animal species, in particular rodents such as a rabbit, rat, or hamster. For example, the antigen-binding region of the selective binding agent of the present invention is preferably derived from a non-human antibody specific for human VGF polypeptide. Preferred sources for the DNA encoding such a non-human antibody include cell lines that produce antibodies, such as hybrid cell lines commonly known as hybridomas.

Selective binding agents such as antibodies and antibody fragments that bind VGF polypeptides are within the scope of the present invention. The antibodies may be polyclonal, including monospecific polyclonal; monoclonal; recombinant; chimeric; humanized, such as CDR-grafted; human; single chain; and/or bispecific; as well as fragments; variants; or derivatives thereof. Antibody fragments include those portions of the antibody that bind to an epitope on the VGF polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies are heterogeneous populations of antibody molecules derived from the sera of animals immunized with an antigen. An antigen is a molecule or a portion of a molecule capable of being bound by an antibody that is additionally capable of inducing an animal to produce antibody capable of binding to an epitope of that antigen. An antigen can have one or more epitopes. The specific reaction referred to above is meant to indicate that the antigen will react, in a highly selective manner, with its corresponding antibody and not with the multitude of other antibodies which can be evoked by other antigens.

Polyclonal antibodies directed toward a VGF polypeptide generally are produced in animals (e.g., rabbits or mice) by means of multiple subcutaneous or intraperitoneal injections of VGF polypeptide and an adjuvant. It may be useful to conjugate a VGF polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-VGF antibody titer.

Monoclonal antibodies contain a substantially homogeneous population of antibodies specific to antigens, which population contains substantially similar epitope binding sites. Such antibodies may be of any immunoglobulin class including IgG, IgM, IgE, IgA, GILD and any subclass thereof. A hybridoma producing a monoclonal antibody of the present invention may be cultivated in vitro, in situ, or in vivo. Production of high titers in vivo or in situ is a preferred method of production.

Monoclonal antibodies directed toward VGF polypeptides are produced using any method that provides for the production of antibody molecules by continuous cell lines in culture. Examples of suitable methods for preparing monoclonal antibodies include the hybridoma methods of Kohler et al., 1975, *Nature* 256:495–97 and the human B-cell hybridoma method (Kozbor, 1984, *J. Immunol.* 133:3001; Brodeur et al., *Monoclonal Antibody Production Techniques and Applications* 51–63 (Marcel Dekker, Inc., 1987). Also provided by the invention are hybridoma cell lines that produce monoclonal antibodies reactive with VGF polypeptides.

Preferred anti-VGF selective binding agents include monoclonal antibodies which will competitively inhibit in vivo the binding to human VGF polypeptide or an antibody having substantially the same specific binding characteristics, as well as fragments and regions thereof. Preferred methods for determining monoclonal antibody specificity and affinity by competitive inhibition can be found in Harlow and Lane, *Antibodies: A Laboratory Manual* (Cold Spring Harbor Laboratories, 1989); *Current Protocols in Immunology* (Colligan et al., eds., Greene Publishing Assoc. and Wiley Interscience, 1993); and Muller, 1988, *Meth. Enzymol.* 92:589–601.

Monoclonal antibodies of the invention may be modified for use as therapeutics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al. 1985, *Proc. Natl. Acad. Sci.* 81:6851–55.

Chimeric antibodies and methods for their production are known in the art. See Cabilly et al., 1984, *Proc. Natl. Acad. Sci. U.S.A.* 81:3273–77; Morrison et al., 1984, *Proc. Natl. Acad. Sci. U.S.A.* 81:6851–55; Boulianne et al., 1984, *Nature* 312:643–46; Neuberger et al., 1985, *Nature* 314: 268–70; Liu et al., 1987, *Proc. Natl. Acad. Sci. U.S.A.* 84:3439–43; and Harlow and Lane, supra.

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is a tetramer ($H_2L_2$) formed by two HL dimers associated through at least one disulfide bridge. A polyvalent chimeric antibody can also be produced, for example, by employing a $C_H$ region that aggregates (e.g., from an IgM H chain or $\mu$ chain).

Chimeric antibodies of the present invention may comprise individual H and/or L immunoglobulin chains. A preferred chimeric H chain comprises an antigen-binding region derived from the H chain of a non-human antibody specific for VGF polypeptide which is linked to at least a portion of a human H chain C region ($C_H$), such as $CH_1$ or $CH_2$. A preferred chimeric L chain comprises an antigen-binding region derived from the L chain of a non-human antibody specific for VGF polypeptide which is linked to at least a portion of a human L chain C region ($C_L$).

Selective binding agents having chimeric H chains and L chains of the same or different variable region binding specificity can also be prepared by appropriate association of the individual polypeptide chains, according to methods known in the art. See e.g., *Current Protocols in Molecular Biology* (Ausubel et al., eds., Green Publishers Inc. and Wiley and Sons 1994) and Harlow et al., supra. Using this approach, host cells expressing chimeric H chains (or their derivatives) are separately cultured from host cells expressing chimeric L chains (or their derivatives), and the immunoglobulin chains are separately recovered and then associated. Alternatively, the host cells can be co-cultured and the chains allowed to associate spontaneously in the culture medium, followed by recovery of the assembled immunoglobulin.

The invention also provides for "derivatives" of selective binding agents, such as antibodies, fragments, regions, or derivatives thereof, which term includes those proteins encoded by truncated or modified genes to yield molecular species functionally resembling immunoglobulin fragments. The modifications include, but are not limited to, addition of genetic sequences coding for cytotoxic proteins such as plant and bacterial toxins. The fragments and derivatives can be produced from any of the host cells of this invention. Alternatively, anti-VGF selective binding agents such as antibodies, fragments and regions thereof can be bound to cytotoxic proteins or compounds in vitro, to provide cytotoxic anti-VGF antibodies which would selectively kill cells having VGF polypeptide receptors.

Suitable fragments include, for example, Fab, Fab', $F(ab')_2$, and Fv. These fragments lack the Fc fragment of an intact antibody, clear more rapidly from the circulation, and can have less non-specific tissue binding than an intact antibody. See Wahl et al., 1983, *J. Nucl. Med.* 24:316–25. These fragments are produced from intact antibodies using methods well known in the art, for example by proteolytic cleavage with enzymes such as papain (to produce Fab fragments) or pepsin (to produce $F(ab')_2$ fragments). The identification of these antigen-binding regions and/or epitopes recognized by monoclonal antibodies of the present invention provides the information necessary to generate additional monoclonal antibodies with similar binding characteristics and therapeutic or diagnostic utility that parallel the embodiments of this application.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, *Nature* 321:522–25; Riechmann et al., 1998, *Nature* 332:323–27; Verhoeyen et al., 1988, *Science* 239:1534–36), by substituting at least a portion of a rodent complementarity-determining region (CDR) for the corresponding regions of a human antibody.

Techniques for creating recombinant DNA versions of the antigen-binding regions of antibody molecules (i.e., Fab or variable region fragments) which bypass the generation of monoclonal antibodies are encompassed within the scope of the present invention. In this technique, antibody-specific messenger RNA molecules are extracted from immune system cells taken from an immunized animal and transcribed into cDNA. The cDNA is then cloned into a bacterial expression system. One example of such a technique suitable for the practice of this invention uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind the antigen. Such VGF-binding molecules (Fab fragments with specificity for VGF polypeptides) are specifically encompassed within the term "antibody" as used herein.

Also within the scope of the invention are techniques developed for the production of chimeric antibodies by splicing the genes from a mouse antibody molecule of appropriate antigen-specificity together with genes from a human antibody molecule of appropriate biological activity (such as the ability to activate human complement and mediate ADCC). Morrison et al., 1984, *Proc. Natl. Acad. Sci. U.S.A.* 81:6851–55; Neuberger et al., 1984, *Nature,*

312:604–08. Selective binding agents such as antibodies produced by this technique are within the scope of the invention.

It will be appreciated that the invention is not limited to mouse or rat monoclonal antibodies; in fact, human antibodies may be used. Such antibodies can be obtained by using human hybridomas. See Cote et al., *Monoclonal Antibodies and Cancer Therapy*, 77 (1985). Fully human antibodies that bind VGF polypeptides are thus encompassed by the invention. Such antibodies are produced by immunizing with a VGF antigen (optionally conjugated to a carrier) transgenic animals (e.g., mice) capable of producing a repertoire of human antibodies in the absence of endogenous immunoglobulin production. See, e.g., Jakobovits et al., 1993, *Proc. Natl. Acad. Sci. U.S.A.* 90:2551–55; Jakobovits et al., 1993, *Nature* 362:255–58; Bruggemann et al., 1993, *Year in Immuno.* 7:33–40.

An antiidiotypic (anti-Id) antibody is an antibody that recognizes unique determinants generally associated with the antigen-binding site of an antibody. An anti-Id antibody can be prepared by immunizing an animal of the same species and genetic type (e.g., mouse strain) as the source of the monoclonal antibody with the monoclonal antibody to which an anti-Id is being prepared. The immunized animal will recognize and respond to the idiotypic determinants of the immunizing antibody by producing an antibody to these idiotypic determinants (the anti-Id antibody). See, e.g., U.S. Pat. No. 4,699,880. The anti-Id antibody may also be used as an "immunogen" to induce an immune response in yet another animal, producing a so-called anti-anti-Id antibody. The anti-anti-Id may be epitopically identical to the original monoclonal antibody that induced the anti-Id. Thus, by using antibodies to the idiotypic determinants of a monoclonal antibody, it is possible to identify other clones expressing antibodies of identical specificity.

Also encompassed by the invention are human antibodies that bind VGF polypeptides. Using transgenic animals (e.g., mice) that are capable of producing a repertoire of human antibodies in the absence of endogenous immunoglobulin production such antibodies are produced by immunization with a VGF polypeptide antigen (i.e., having at least 6 contiguous amino acids), optionally conjugated to a carrier. See, e.g., Jakobovits et al., 1993, *Proc. Natl. Acad. Sci.* 90:2551–55; Jakobovits et al., 1993, *Nature* 362:255–58; Bruggermann et al., 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then crossbred to obtain an animal having all of the desired immune system modifications. When administered an immunogen, these transgenic animals produce antibodies with human (rather than, e.g., murine) amino acid sequences, including variable regions which are immunospecific for these antigens. See PCT App. Nos. PCT/US96/05928 and PCT/US93/06926. Additional methods are described in U.S. Pat. No. 5,545,807, PCT App. Nos. PCT/US91/245 and PCT/GB89/01207, and in EP Pub. Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in PCT App. No. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein and known in the art. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-VGF antibodies of the invention may be employed in any known assay method, such as competitive binding assays, direct and indirect sandwich assays, and immunoprecipitation assays (Sola, *Monoclonal Antibodies: A Manual of Techniques* 147–158 (CRC Press, Inc., 1987)) for the detection and quantitation of VGF polypeptides. The antibodies will bind VGF polypeptides with an affinity that is appropriate for the assay method being employed.

For diagnostic applications, in certain embodiments, anti-VGF antibodies may be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, $^{125}$I, $^{99}$Tc, $^{111}$In, or $^{67}$Ga; a fluorescent or chemiluminescent compound, such as fluorescein isothiocyanate, rhodamine, or luciferin; or an enzyme, such as alkaline phosphatase, β-galactosidase, or horseradish peroxidase (Bayer, et al., 1990, *Meth. Enz.* 184:138–63).

Competitive binding assays rely on the ability of a labeled standard (e.g., a VGF polypeptide, or an immunologically reactive portion thereof) to compete with the test sample analyte (a VGF polypeptide) for binding with a limited amount of anti-VGF antibody. The amount of a VGF polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-VGF antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a VGF polypeptide. In one embodiment, antagonist antibodies of the invention are antibodies or binding fragments thereof which are capable of specifically binding to a VGF polypeptide and which are capable of inhibiting or eliminating the functional activity of a VGF polypeptide in vivo or in vitro. In preferred embodiments, the selective binding agent, e.g., an antagonist antibody, will inhibit the functional activity of a VGF polypeptide by at least about 50%, and preferably by at least about 80%. In another embodiment, the selective binding agent may be an anti-VGF polypeptide antibody that is capable of interacting with a VGF polypeptide binding partner (a ligand or receptor) thereby inhibiting or eliminating VGF polypeptide activity in vitro or in vivo. Selective binding agents, including agonist and antagonist anti-VGF polypeptide antibodies, are identified by screening assays that are well known in the art.

The invention also relates to a kit comprising VGF selective binding agents (such as antibodies) and other reagents useful for detecting VGF polypeptide levels in biological samples. Such reagents may include a detectable label, blocking serum, positive and negative control samples, and detection reagents.

Chemical Derivatives

Chemically modified derivatives of VGF polypeptides may be prepared by one skilled in the art, given the disclosures described herein. VGF polypeptide derivatives are modified in a manner that is different—either in the type or location of the molecules naturally attached to the polypeptide. Derivatives may include molecules formed by the deletion of one or more naturally-attached chemical groups. VGF polypeptides may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$–$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules which may be used to prepare covalently attached VGF polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby a VGF polypeptide becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the VGF polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4–10; EP Pub. Nos. 154316 and 401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$–$C_{10}$ alkoxy or aryloxy derivatives thereof (see U.S. Pat. No. 5,252,714).

In another embodiment, VGF polypeptides may be chemically coupled to biotin. The biotin/VGF polypeptide molecules are then allowed to bind to avidin, resulting in tetravalent avidin/biotin/VGF polypeptide molecules. VGF polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present VGF polypeptide derivatives include those described herein for VGF polypeptides. However, the VGF polypeptide derivatives disclosed herein may have additional activities, enhanced or reduced biological activity, or other characteristics, such as increased or decreased half-life, as compared to the non-derivatized molecules.

Assaying for Other Modulators of VGF Polypeptide Activity

In some situations, it may be desirable to identify molecules that are modulators, i.e., agonists or antagonists, of the activity of VGF polypeptide. Natural or synthetic molecules that modulate VGF polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of a VGF polypeptide. Most commonly, a test molecule will interact directly with a VGF polypeptide. However, it is also contemplated that a test molecule may also modulate VGF polypeptide activity indirectly, such as by affecting VGF gene expression, or by binding to a VGF polypeptide binding partner (e.g., receptor or ligand). In one embodiment, a test molecule will bind to a VGF polypeptide with an affinity constant of at least about $10^{-6}$ M, preferably about $10^{-8}$ M, more preferably about $10^{-9}$ M, and even more preferably about $10^{-10}$ M.

A VGF polypeptide agonist or antagonist may be a protein, peptide, carbohydrate, lipid, or small molecular weight molecule that interacts with VGF polypeptide to regulate its activity. Molecules which regulate VGF polypeptide expression include nucleic acids which are complementary to nucleic acids encoding a VGF polypeptide, or are complementary to nucleic acids sequences which direct or control the expression of VGF polypeptide, and which act as anti-sense regulators of expression.

Once a test molecule has been identified as interacting with a VGF polypeptide, the molecule may be further evaluated for its ability to increase or decrease VGF polypeptide activity. The measurement of the interaction of a test molecule with VGF polypeptide may be carried out in several formats, including cell-based binding assays, membrane binding assays, solution-phase assays, and immunoassays. In general, a test molecule is incubated with a VGF polypeptide for a specified period of time, and VGF polypeptide activity is determined by one or more assays for measuring biological activity.

The interaction of test molecules with VGF polypeptides may also be assayed directly using polyclonal or monoclonal antibodies in an immunoassay. Alternatively, modified forms of VGF polypeptides containing epitope tags as described herein may be used in solution and immunoassays.

In the event that VGF polypeptides display biological activity through an interaction with a binding partner (e.g., a receptor or a ligand), a variety of in vitro assays may be used to measure the binding of a VGF polypeptide to the corresponding binding partner (such as a selective binding agent, receptor, or ligand). These assays may be used to screen test molecules for their ability to increase or decrease the rate and/or the extent of binding of a VGF polypeptide to its binding partner. In one assay, a VGF polypeptide is immobilized in the wells of a microtiter plate. Radiolabeled VGF polypeptide binding partner (for example, iodinated VGF polypeptide binding partner) and a test molecule can then be added either one at a time (in either order) or simultaneously to the wells. After incubation, the wells can be washed and counted for radioactivity, using a scintillation counter, to determine the extent to which the binding partner bound to the VGF polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing VGF polypeptide binding partner to the microtiter plate wells, incubating with the test molecule and radiolabeled VGF polypeptide, and determining the extent of VGF polypeptide binding. See, e.g., *Current Protocols in Molecular Biology*, chap. 18 (Ausubel et al., eds., Green Publishers Inc. and Wiley and Sons 1995).

As an alternative to radiolabeling, a VGF polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to a VGF polypeptide or to a VGF polypeptide binding partner, and which is conjugated to biotin, may also be used for purposes of detection following incubation of the complex with enzyme-linked streptavidin linked to AP or HRP.

A VGF polypeptide or a VGF polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between a VGF polypeptide and its binding partner can be assessed using the methods described herein. Alternatively, the substrate-protein complex can be immobilized in a column with the test molecule and complementary protein passing through the column. The formation of a complex between a VGF polypeptide and its binding partner can then be assessed using any of the techniques described herein (e.g., radiolabelling or antibody binding).

Another in vitro assay that is useful for identifying a test molecule which increases or decreases the formation of a complex between a VGF polypeptide binding protein and a VGF polypeptide binding partner is a surface plasmon resonance detector system such as the BIAcore assay system (Pharmacia, Piscataway, N.J.). The BIAcore system is utilized as specified by the manufacturer. This assay essentially involves the covalent binding of either VGF polypeptide or a VGF polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between a VGF polypeptide and a VGF polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between a VGF polypeptide and VGF polypeptide binding partner. The assays may be automated to screen compounds generated in phage display, synthetic peptide, and chemical synthesis libraries.

Compounds which increase or decrease the formation of a complex between a VGF polypeptide and a VGF polypeptide binding partner may also be screened in cell culture using cells and cell lines expressing either VGF polypeptide or VGF polypeptide binding partner. Cells and cell lines may be obtained from any mammal, but preferably will be from human or other primate, canine, or rodent sources. The binding of a VGF polypeptide to cells expressing VGF polypeptide binding partner at the surface is evaluated in the presence or absence of test molecules, and the extent of binding may be determined by, for example, flow cytometry using a biotinylated antibody to a VGF polypeptide binding partner. Cell culture assays can be used advantageously to further evaluate compounds that score positive in protein binding assays described herein.

Cell cultures can also be used to screen the impact of a drug candidate. For example, drug candidates may decrease or increase the expression of the VGF gene. In certain embodiments, the amount of VGF polypeptide or a VGF polypeptide fragment that is produced may be measured after exposure of the cell culture to the drug candidate. In certain embodiments, one may detect the actual impact of the drug candidate on the cell culture. For example, the over-expression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al., 1994, *Proc. Natl. Acad. Sci. U.S.A.* 91:664–68. For example, an 11 amino acid sequence (Y-G-R-K-K-R-R-Q-R-R-R; SEQ ID NO: 11) of the HIV tat protein (termed the "protein transduction domain," or TAT PDT) has been described as mediating delivery across the cytoplasmic membrane and the nuclear membrane of a cell. See Schwarze et al., 1999, *Science* 285:1569–72; and Nagahara et al., 1998, *Nat. Med.* 4:1449–52. In these procedures, FITC-constructs (FITC-labeled G-G-G-G-Y-G-R-K-K-R-R-Q-R-R-R; SEQ ID NO: 12), which penetrate tissues following intraperitoneal administration, are prepared, and the binding of such constructs to cells is detected by fluorescence-activated cell sorting (FACS) analysis. Cells treated with a tat-β-gal fusion protein will demonstrate β-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, a VGF antagonist (such as an anti-VGF selective binding agent, small molecule, soluble receptor, or antisense oligonucleotide) can be administered intracellularly to inhibit the activity of a VGF molecule. As used herein, the term "VGF molecule" refers to both VGF nucleic acid molecules and VGF polypeptides as defined herein. Where desired, the VGF protein itself may also be internally administered to a cell using these procedures. See also, Straus, 1999, *Science* 285:1466–67.

Therapeutic Uses

The VGF polypeptides and selective binding agents of the present invention can be used to treat, diagnose, ameliorate, or prevent a number of acute and chronic diseases or conditions, including those recited herein.

VGF-related diseases, conditions, and disorders include obesity, sterility, cachexia, eating disorders, AIDS-related complex, hypermetabolic conditions, hyperactivity, hypoactivity, and hyperinsulin production.

Other diseases caused by or mediated by undesirable levels of VGF polypeptides are encompassed within the scope of the invention. Undesirable levels include excessive levels of VGF polypeptides and sub-normal levels of VGF polypeptides.

VGF Polypeptide Compositions and Administration

Therapeutic compositions are within the scope of the present invention. Such VGF polypeptide pharmaceutical compositions may comprise a therapeutically effective amount of a VGF polypeptide in admixture with a pharmaceutically or physiologically acceptable formulation agent selected for suitability with the mode of administration. Pharmaceutical compositions may comprise a therapeutically effective amount of one or more VGF polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences* (18th Ed., A. R. Gennaro, ed., Mack Publishing Company 1990.

The optimal pharmaceutical composition will be determined by a skilled artisan depending upon, for example, the intended route of administration, delivery format, and desired dosage. See, e.g., *Remington's Pharmaceutical Sciences*, supra. Such compositions may influence the physical state, stability, rate of in vivo release, and rate of in vivo clearance of the VGF molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0–8.5, or acetate buffer of about pH 4.0–5.5, which may further include sorbitol or a suitable substitute. In one embodiment of the present invention, VGF polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the VGF polypeptide product may be formulated as a lyophilizate using appropriate excipients such as sucrose.

The VGF polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired VGF molecule in a pharmaceutically acceptable vehicle. A particularly suitable vehicle for parenteral injection is sterile distilled water in which a VGF molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, VGF polypeptide may be formulated as a dry powder for inhalation. VGF polypeptide or nucleic acid molecule inhalation solutions may also be formulated with a propellant for aerosol delivery. In yet another embodiment, solutions may be nebulized. Pulmonary administration is further described in PCT Pub. No. WO 94/20069, which describes the pulmonary delivery of chemically modified proteins.

It is also contemplated that certain formulations may be administered orally. In one embodiment of the present invention, VGF polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the VGF polypeptide. Diluents, flavorings, low melting point waxes, vegetable oils, lubricants, suspending agents, tablet disintegrating agents, and binders may also be employed.

Another pharmaceutical composition may involve an effective quantity of VGF polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional VGF polypeptide pharmaceutical compositions will be evident to those skilled in the art, including formulations involving VGF polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., PCT/US93/00829, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and EP Pub. No. 058481), copolymers of L-glutamic acid and gamma ethyl-L-glutamate (Sidman et al., 1983, *Biopolymers* 22:547–56), poly(2-hydroxyethyl-methacrylate) (Langer et al., 1981, *J. Biomed. Mater. Res.* 15:167–277 and Langer, 1982, *Chem. Tech.* 12:98–105), ethylene vinyl acetate (Langer et al., supra) or poly-D(−)-3-hydroxybutyric acid (EP Pub. No. 133988). Sustained-release compositions may also include liposomes, which can be prepared by any of several methods known in the art. See, e.g., Eppstein et al., 1985, *Proc. Natl. Acad. Sci. USA* 82:3688–92; and EP Pub. Nos. 036676, 088046, and 143949.

The VGF pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of a VGF pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the VGF molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 μg/kg to up to about 100 mg/kg or more, depending on the factors mentioned above. In other embodiments, the dosage may range from 0.1 μg/kg up to about 100 mg/kg; or 1 μg/kg up to about 100 mg/kg; or 5 μg/kg up to about 100 mg/kg.

The frequency of dosing will depend upon the pharmacokinetic parameters of the VGF molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use VGF polypeptide pharmaceutical compositions in an ex vivo manner. In such instances, cells, tissues, or organs that have been removed from the patient are exposed to VGF polypeptide pharmaceutical compositions after which the cells, tissues, or organs are subsequently implanted back into the patient.

In other cases, a VGF polypeptide can be delivered by implanting certain cells that have been genetically engineered, using methods such as those described herein, to express and secrete the VGF polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more VGF polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent VGF gene, or an underexpressed gene, and thereby produce a cell which expresses therapeutically efficacious amounts of VGF polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419–28; Thomas and Capecchi, 1987, *Cell* 51:503–12; Doetschman et al., 1988, *Proc. Natl. Acad. Sci. U.S.A.* 85:8583–87) or to correct specific mutations within defective genes (Doetschman et al., 1987, *Nature* 330:576–78). Exemplary homologous recombination techniques are described in U.S. Pat. No. 5,272,071; EP Pub. Nos. 9193051 and 505500; PCT/US90/07642, and PCT Pub No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of a VGF polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired VGF polypeptide. The control element controls a portion of the DNA present in the host cell genome. Thus, the expression of the desired VGF polypeptide may be achieved not by transfection of DNA that encodes the VGF gene itself, but rather by the use of targeting DNA (containing regions of homology with the endogenous gene of interest) coupled with DNA regulatory segments that provide the endogenous gene sequence with recognizable signals for transcription of a VGF gene.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, VGF polypeptide production from a cell's endogenous VGF gene involves first using homologous recombination to place a recombination sequence from a site-specific recombination system (e.g., Cre/loxP, FLP/FRT) (Sauer, 1994, *Curr. Opin. Biotechnol.*, 5:521–27; Sauer, 1993, *Methods Enzymol.*, 225:890–900) upstream of (i.e., 5' to) the cell's endogenous genomic VGF polypeptide coding region. A plasmid containing a recombination site homologous to the site that was placed just upstream of the genomic VGF polypeptide coding region is introduced into the modified cell line along with the appropriate recombinase enzyme. This recombinase causes the plasmid to integrate, via the plasmid's recombination site, into the recombination site located just upstream of the genomic VGF polypeptide coding region in the cell line (Baubonis and Sauer, 1993, *Nucleic Acids Res.* 21:2025–29; O'Gorman et al., 1991, *Science* 251:1351–55). Any flanking sequences known to increase transcription (e.g., enhancer/promoter, intron, translational enhancer), if properly positioned in this plasmid, would integrate in such a manner as to create a new or modified transcriptional unit resulting in de novo or increased VGF polypeptide production from the cell's endogenous VGF gene.

A further method to use the cell line in which the site specific recombination sequence had been placed just upstream of the cell's endogenous genomic VGF polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.*, 5:521–27; Sauer, 1993, *Methods Enzymol.*, 225:890–900) that would create a new or modified transcriptional unit resulting in de novo or increased VGF polypeptide production from the cell's endogenous VGF gene.

An additional approach for increasing, or causing, the expression of VGF polypeptide from a cell's endogenous VGF gene involves increasing, or causing, the expression of a gene or genes (e.g., transcription factors) and/or decreasing the expression of a gene or genes (e.g., transcriptional repressors) in a manner which results in de novo or increased VGF polypeptide production from the cell's endogenous VGF gene. This method includes the introduction of a non-naturally occurring polypeptide (e.g., a polypeptide comprising a site specific DNA binding domain fused to a transcriptional factor domain) into the cell such that de novo or increased VGF polypeptide production from the cell's endogenous VGF gene results.

VGF polypeptide cell therapy, e.g., the implantation of cells producing VGF polypeptides, is also contemplated. This embodiment involves implanting cells capable of synthesizing and secreting a biologically active form of VGF polypeptide. Such VGF polypeptide-producing cells can be cells that are natural producers of VGF polypeptides or may be recombinant cells whose ability to produce VGF polypeptides has been augmented by transformation with a gene encoding the desired VGF polypeptide or with a gene augmenting the expression of VGF polypeptide. Such a modification may be accomplished by means of a vector suitable for delivering the gene as well as promoting its expression and secretion. In order to minimize a potential immunological reaction in patients being administered a VGF polypeptide, as may occur with the administration of a polypeptide of a foreign species, it is preferred that the natural cells producing VGF polypeptide be of human origin and produce human VGF polypeptide. Likewise, it is preferred that the recombinant cells producing VGF polypeptide be transformed with an expression vector containing a gene encoding a human VGF polypeptide.

Implanted cells may be encapsulated to avoid the infiltration of surrounding tissue. Human or non-human animal cells may be implanted in patients in biocompatible, semipermeable polymeric enclosures or membranes that allow the release of VGF polypeptide, but that prevent the destruction of the cells by the patient's immune system or by other detrimental factors from the surrounding tissue. Alternatively, the patient's own cells, transformed to produce VGF polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (PCT Pub. No. WO 95/05452 and PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in PCT Pub. No. WO 91/10425 (Aebischer et al.). See also, PCT Pub. No. WO 91/10470 (Aebischer et al.); Winn et al., 1991, *Exper. Neurol.* 113:322–29; Aebischer et al., 1991, *Exper. Neurol.* 111:269–75; and Tresco et al., 1992, *ASAIO* 38:17–23.

In vivo and in vitro gene therapy delivery of VGF polypeptides is also envisioned. One example of a gene therapy technique is to use a nucleic acid (either genomic DNA, cDNA, and/or synthetic DNA) encoding a VGF polypeptide which may be operably linked to a constitutive or inducible promoter to form a "gene therapy DNA construct." The promoter may be homologous or heterologous to the endogenous VGF gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the VGF gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see PCT Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al., 2000, *Science* 287:816–17 and Rivera et al., 2000, *Science* 287:826–30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and PCT Pub. Nos. WO 96/40911 and WO 97/10337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA-binding domain, and ligand-binding domain to initiate transcription. The ecdysone system is further described in U.S. Pat. No. 5,514,578 and PCT Pub. Nos. WO 97/38117, WO 96/37609, and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing a nucleic acid molecule encoding VGF polypeptide into cells via local injection or by other appropriate viral or non-viral delivery vectors. Hefti, 1994, *Neurobiology* 25:1418–35. For example, a nucleic acid molecule encoding a VGF polypeptide may be contained in an adeno-associated virus (AAV) vector for delivery to the targeted cells (see, e.g., Johnson, PCT Pub. No. WO 95/34670; PCT App. No. PCT/US95/07178). The recombinant AAV genome typically contains AAV inverted terminal repeats flanking a DNA sequence encoding a VGF polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 (involving adenoviral vectors), U.S. Pat. No. 5,672,510 (involving retroviral vectors), U.S. Pat. No. 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and PCT Pub. No. WO 96/40958 (involving nuclear ligands).

It is also contemplated that VGF gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous VGF polypeptide expression in a cell via gene therapy is to insert one or more enhancer elements into the VGF polypeptide promoter, where the enhancer elements can serve to increase transcriptional activity of a VGF gene. The enhancer elements used will be selected based on the tissue in which one desires to activate the gene-enhancer elements known to confer promoter activation in that tissue will be selected. For example, if a gene encoding a VGF polypeptide is to be "turned on" in T-cells, the ick promoter enhancer element may be used. Here, the functional portion of the transcriptional element to be added may be inserted into a fragment of DNA containing the VGF polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease VGF polypeptide expression by modifying the nucleotide sequence of the endogenous promoter. Such modification is typically accomplished via homologous recombination methods. For example, a DNA molecule containing all or a portion of the promoter of the VGF gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding VGF gene. The deletion of the TATA box or the transcription activator binding site in the promoter may be accomplished by generating a DNA construct comprising all or the relevant portion of the VGF polypeptide promoter (from the same or a related species as the VGF gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Uses of VGF Polypeptides

VGF polypeptides may be used (simultaneously or sequentially) in combination with one or more cytokines, growth factors, antibiotics, anti-inflammatories, and/or chemotherapeutic agents as is appropriate for the condition being treated.

Other methods may also be employed where it is desirable to inhibit the activity of one or more VGF polypeptides. Such inhibition may be effected by nucleic acid molecules that are complementary to and hybridize to expression control sequences (triple helix formation) or to VGF mRNA. For example, antisense DNA or RNA molecules, which have a sequence that is complementary to at least a portion of a VGF gene can be introduced into the cell. Anti-sense probes may be designed by available techniques using the sequence of the VGF gene disclosed herein. Typically, each such antisense molecule will be complementary to the start site (5' end) of each selected VGF gene. When the antisense molecule then hybridizes to the corresponding VGF mRNA, translation of this mRNA is prevented or reduced. Anti-sense inhibitors provide information relating to the decrease or absence of a VGF polypeptide in a cell or organism.

Alternatively, gene therapy may be employed to create a dominant-negative inhibitor of one or more VGF polypeptides. In this situation, the DNA encoding a mutant polypeptide of each selected VGF polypeptide can be prepared and introduced into the cells of a patient using either viral or non-viral methods as described herein. Each such mutant is typically designed to compete with endogenous polypeptide in its biological role.

In addition, a VGF polypeptide, whether biologically active or not, may be used as an immunogen, that is, the polypeptide contains at least one epitope to which antibodies may be raised. Selective binding agents that bind to a VGF polypeptide (as described herein) may be used for in vivo and in vitro diagnostic purposes, including, but not limited to, use in labeled form to detect the presence of VGF polypeptide in a body fluid or cell sample. The antibodies may also be used to prevent, treat, or diagnose a number of diseases and disorders, including those recited herein. The antibodies may bind to a VGF polypeptide so as to diminish or block at least one activity characteristic of a VGF polypeptide, or may bind to a polypeptide to increase at least one activity characteristic of a VGF polypeptide (including by increasing the pharmacokinetics of the VGF polypeptide).

The VGF polypeptides of the present invention can be used to clone VGF polypeptide receptors, using an expression cloning strategy. Radiolabeled (125-Iodine) VGF polypeptide or affinity/activity-tagged VGF polypeptide (such as an Fc fusion or an alkaline phosphatase fusion) can be used in binding assays to identify a cell type or cell line or tissue that expresses VGF polypeptide receptors. RNA isolated from such cells or tissues can be converted to cDNA, cloned into a mammalian expression vector, and transfected into mammalian cells (such as COS or 293 cells) to create an expression library. A radiolabeled or tagged VGF polypeptide can then be used as an affinity ligand to identify and isolate from this library the subset of cells that express the VGF polypeptide receptors on their surface. DNA can then be isolated from these cells and transfected into mammalian cells to create a secondary expression library in which the fraction of cells expressing VGF polypeptide receptors is many-fold higher than in the original library. This enrichment process can be repeated iteratively until a single recombinant clone containing a VGF polypeptide receptor is isolated. Isolation of the VGF polypeptide receptors is useful for identifying or developing novel agonists and antagonists of the VGF polypeptide signaling pathway. Such agonists and antagonists include soluble VGF polypeptide receptors, anti-VGF polypeptide receptor antibodies, small molecules, or antisense oligonucleotides, and they may be used for treating, preventing, or diagnosing one or more of the diseases or disorders described herein.

The following examples are intended for illustration purposes only, and should not be construed as limiting the scope of the invention in any way.

EXAMPLE 1

Production of Anti-VGF Polypeptide Antibodies

Antibodies against VGF polypeptides were produced by injecting rabbits with VGF polypeptides synthesized by the Amgen Boulder Peptide Technology group using standard peptide synthesis protocols. Following peptide synthesis, VGF polypeptides from different batches were pooled and lyophilized. The peptide content for each VGF polypeptide was determined by hydrolysis with HCl.

To prepare polyclonal anti-VGF polypeptide antibodies from VGF polypeptides (VGF-1; SEQ ID NO: 1 or VGF-2; SEQ ID NO: 4; Table I) lacking cysteine residues, 5 mg of a VGF polypeptide and 0.5 ml of Imject® EDC Conjugation Buffer (Pierce, Rockford, Ill.) were transferred to a 2 ml vial, and the mixture was vortexed. A 20 mg vial of Imject® Keyhole Limpet Hemocyanin (Pierce) was diluted in 2 ml sterilized water, and 0.5 ml of this solution was added to the VGF polypeptide solution. Following the addition of Keyhole Limpet Hemocyanin, 0.1 ml of EDC (10 mg of EDC (Pierce) in 1 ml sterilized water) was added to the VGF polypeptide and this solution was incubated at room temperature for at least 2 hours.

Following incubation, conjugated VGF polypeptide was transferred to Spectra/Por 6 dialysis tubing (Spectrum Laboratories, Rancho Dominguez, Calif.), having a molecular weight cut-off of 1000, and dialyzed in 2 L of PBS overnight at 4° C. to remove EDTA, which is a known anti-coagulant, from the sample. The dialyzed, conjugated VGF polypeptide solution was transferred to a 15 ml conical tube and PBS was added to bring the volume of the solution up to 4 ml. Aliquots of 1 ml each were transferred to 2 ml screw-top tubes, each aliquot was drawn into a 2 ml glass syringe, and then 1 ml of Titermax® Research Adjuvant (CytRx, Norcross, Ga.) was drawn.

The syringe was connected with an 18-gauge mixing needle and the solution was mixed to emulsify. The mixture was then transferred to two 1 ml syringes for intramuscular injection into rabbits. Rabbits were injected with 0.1 ml of VGF polypeptide/adjuvant solution at 2 injection sites, and the rabbits were then boosted at 4 weeks and 6 weeks thereafter. Rabbits were test bled (removing approximately 5 ml) following the second boost and then test bled again after two weeks. If the production bleeds were deemed acceptable, rabbits were boosted again and then bled once a week for six weeks (removing approximately 40 ml) two weeks after this boost.

To prepare polyclonal anti-VGF polypeptide antibodies from VGF polypeptides possessing cysteine residues, 5 mg of a VGF polypeptide and 0.5 ml of Imject® Maleimide Conjugation Buffer (Pierce) were transferred to a 2 ml vial, and the mixture was vortexed. A 20 mg vial of Imject® Keyhole Limpet Hemocyanin (Pierce) was diluted in 2 ml sterilized water, and 0.5 ml of this solution was added to the VGF polypeptide solution. Following the addition of Keyhole Limpet Hemocyanin, the VGF polypeptide solution was incubated at room temperature for at least 2 hours.

Following incubation, conjugated VGF polypeptide was transferred to Spectra/Por 6 dialysis tubing and dialyzed in 2 L of PBS overnight at 4° C. to remove EDTA from the sample. The dialyzed, conjugated VGF polypeptide solution was transferred to a 15 ml conical tube and PBS was added to bring the volume of the solution up to 4 ml. Aliquots of 1 ml each were transferred to 2 ml screw-top tubes, each aliquot was drawn into a 2 ml glass syringe, and then 1 ml of Titermax® Research Adjuvant (CytRx) was drawn.

The syringe was connected with an 18-gauge mixing needle and the solution was mixed to emulsify. The mixture was then transferred to two 1 ml syringes for intramuscular injection into rabbits. Rabbits were injected with 0.1 ml of VGF polypeptide/adjuvant solution at 2 injection sites, and the rabbits were then boosted at 4 weeks and 6 weeks thereafter. Rabbits were test bled (removing approximately 5 ml) following the second boost and then test bled again after two weeks. If the production bleeds were deemed acceptable, rabbits were boosted again and then bled once a week for six weeks (removing approximately 40 ml) two weeks after this boost. FIGS. 2 and 3 illustrate the antibody titer levels of rabbits injected with either VGF-1 or VGF-2.

EXAMPLE 2

Biological Activity of VGF Polypeptide in Knockout Mice

The biological activity of VGF polypeptides in knockout mice was analyzed using VGF polypeptides synthesized by the Amgen Boulder Peptide Technology group using standard peptide synthesis protocols. Following peptide synthesis, VGF polypeptides from different batches were pooled and lyophilized. The peptide content for each VGF polypeptide was determined by hydrolysis with HCl.

VGF gene knockout mice were obtained from Steve Salton of Mt. Sinai School of Medicine, New York, N.Y. Prior to administration of VGF polypeptide, knockout mice were housed under LD 12:12 conditions (i.e., 12 hours of light and 12 hours of dark). Twenty-four hours before VGF polypeptide injection, knockout mice were individually caged and moved to a temporary housing room where the mice were kept for the remainder of the experiment under LD 12:12 conditions.

VGF polypeptide was administered to knockout mice twice daily (at 9:00 a.m. and 6:00 p.m.) by intraperitoneal injection of 2 mg of VGF-1a (SEQ ID NO: 2; Table I). Prior to injection, VGF-1a polypeptide was diluted to 16% in aCSF Solution Buffer (126.6 mM NaCl, 2.6 mM KCl, 2.0 mM $MgCl_2$ and 1.4 mM $CaCl_2$, 10 mM $NaPO_4$, pH 7.4). Knockout mice were administered VGF-1a polypeptide for five days and the body weight of each mouse was measured daily. The body weight of treated mice was measured daily for three days following the withdrawal of VGF-1a polypeptide.

FIG. 1 illustrates the body weight of VGF knockout mice following administration of VGF-1a. Three of the four treated mice gained 10–15 percent in body weight. From this experiment, it was not possible to determine whether the increase in weight was a result of an increased uptake of food or water.

EXAMPLE 3

VGF Polypeptide-Fc Fusion Proteins

VGF polypeptides are expressed as fusion proteins with a human immunoglobulin IgG heavy chain Fc region at their carboxyl- or amino-terminus. Using appropriate PCR primers and standard PCR amplification procedures, VGF polypeptide-Fc fusion constructs are prepared by fusing in-frame a DNA sequence coding for the Fc region of human IgG1 with that encoding VGF-1 (SEQ ID NO: 1), VGF-1b (SEQ ID NO: 3), or VGF-2 (SEQ ID NO: 4) polypeptide.

VGF polypeptide-Fc fusion products generated by PCR are digested with the restriction endonucleases Nde I and Bam HI, ligated into the vector pAMG21, and then transformed into competent *E. coli* strain 2596 cells using standard techniques. Clones are screened for the ability to produce the recombinant protein product and to possess the gene fusion having the correct nucleotide sequence.

Bacterial cultures containing the Fc fusion constructs in the *E. coli* strain GM221 are grown at 37° C. in Luria Broth medium containing 50 mg/ml kanamycin. Induction of gene product expression from the luxPR promoter is achieved following the addition of the synthetic autoinducer N-(3-oxohexanoyl)-DL-homoserine lactone to the culture media to a final concentration of 20 ng/ml. Cultures are incubated at 37° C. for an additional 3 hours. Following this incubation, the bacterial cultures are examined by microscopy for the presence of inclusion bodies and are then collected by centrifugation. Cell pellets are lysed directly by resuspension in Laemmli sample buffer containing 10% β-mercaptoethanol and are analyzed by SDS-PAGE.

VGF polypeptide-Fc fusion proteins are purified by first disrupting the cells in water using high pressure homogenization (i.e., 2 passes at 14,000 PSI). Inclusion bodies are harvested by centrifugation at 4200 RPM in J-6B for 1 hour and the inclusion bodies are solubilized in 6M guanidine, 50 mM Tris, 8 mM DTT, pH 8.7 for 1 hour at a 1/10 ratio. The solubilized mixture is then diluted 20 times into 2 M urea, 50 mM Tris, 160 mM arginine, 3 mM cysteine, pH 8.5. The mixture is stirred overnight in the cold, concentrated about 10 fold by ultafiltration, and then diluted 3 fold with 10 mM Tris, 1.5 M urea, pH 9. The pH of this mixture is then adjusted to pH 5 with acetic acid. The precipitate is removed by centrifugation and the supernatant is loaded onto a SP-Sepharose Fast Flow column equilibrated in 20 mM NaAc, 100 mM NaCl, pH 5 (10 mg/ml protein load; room temperature). The protein is eluted from the column using a 20-column volume gradient in the same buffer ranging from 100 mM NaCl to 500 mM NaCl. The pool from the column is diluted 3 fold and loaded onto a SP-Sepharose HP column in 20 mM NaAc, 150 mM NaCl, pH 5(10 mg/ml protein load; room temperature). The protein is eluted using a 20-column volume gradient in the same buffer ranging from 150 mM NaCl to 400 mM NaCl. The peak is pooled and filtered.

VGF polypeptide-Fc fusion protein activity is assessed using methods described herein or known to one of ordinary skill in the art.

EXAMPLE 4

Expression of Murine VGF Polypeptide in Transgenic Mice

To assess the biological activity of VGF polypeptide, a construct encoding a murine VGF polypeptide under the control of the synapsin promoter was prepared using standard protocols. The delivery of this construct is expected to cause pathological changes that are informative as to the function of VGF polypeptide. Similarly, a construct containing the full-length VGF polypeptide under the control of the beta actin promoter was prepared using standard protocols. The delivery of this construct is expected to result in ubiquitous expression.

To generate these constructs, PCR was used to amplify template DNA sequences encoding murine VGF polypeptide using primers that correspond to the 5' and 3' ends of the desired sequence and which incorporate restriction enzyme sites to permit insertion of the amplified product into an expression vector. Following amplification, PCR products were gel purified, digested with the appropriate restriction enzymes, and ligated into an expression vector using standard recombinant DNA techniques. See Graham et al., 1997, *Nature Genetics*, 17:272–74 and Ray et al., 1991, *Genes Dev.* 5:2265–73.

Following ligation, reaction mixtures were used to transform an *E. coli* host strain by electroporation and transformants were selected for drug resistance. Plasmid DNA from selected colonies was isolated and subjected to DNA sequencing to confirm the presence of an appropriate insert and absence of mutation. The VGF polypeptide expression vectors were purified through two rounds of CsCl density gradient centrifugation, cleaved with a suitable restriction enzyme, and the linearized fragment containing the murine VGF polypeptide transgene was purified by gel electrophoresis. The purified fragment was resuspended in 5 mM Tris, pH 7.4, and 0.2 mM EDTA at a concentration of 2 µg/mL.

Single-cell embryos from BDF1×BDF1 bred mice were injected as described (PCT Pub. No. WO 97/23614). Embryos were cultured overnight in a $CO_2$ incubator and 15–20 two-cell embryos were transferred to the oviducts of a pseudopregnant CD1 female mice. Offspring obtained from the implantation of microinjected embryos were screened by PCR amplification of the integrated transgene in genomic DNA samples as follows. Ear pieces were digested in 20 µL ear buffer (20 mM Tris, pH 8.0, 10 mM EDTA, 0.5% SDS, and 500 mg/mL proteinase K) at 55° C. overnight. The sample was then diluted with 200 µL of TE, and 2 µL of the ear sample was used in a PCR reaction using appropriate primers.

Transgenic founder animals were identified and used to generate F1 mice. To do this, portions of the spleen, liver, and total brain from F1 mice are removed and total cellular RNA isolated from the spleens using the Total RNA Extraction Kit (Qiagen) and transgene expression determined by RT-PCR. RNA recovered from spleens is converted to cDNA using the SuperScript Preamplification System (Gibco-BRL) as follows. A suitable primer, located in the expression vector sequence and 3' to the VGF polypeptide transgene, is used to prime cDNA synthesis from the transgene transcripts. Ten mg of total RNA prepared from the liver, brain, and spleen tissue of transgenic founders and controls is incubated with 1 mM of primer for 10 minutes at 70° C. and placed on ice. The reaction is then supplemented with 10 mM Tris-HCl, pH 8.3, 50 mM KCl, 2.5 mM $MgCl_2$, 10 mM of each dNTP, 0.1 mM DTT, and 200 U of SuperScript II reverse transcriptase. Following incubation for 50 minutes at 42° C., the reaction is stopped by heating for 15 minutes at 72° C. and digested with 2U of RNase H for 20 minutes at 37° C. Samples are then amplified by PCR using primers specific for murine VGF polypeptide.

The littermates from transgenic positive F1 mice are crossbred to generate F2 homozygous mice. The expression level of VGF mRNA in F2 mice is determined as described herein.

EXAMPLE 5

Biological Activity of Murine VGF Polypeptide in F2 Transgenic Mice

Prior to euthanasia, F2 transgenic animals obtained in Example 4 are weighed, anesthetized by isofluorane and blood drawn by cardiac puncture. The samples are subjected to hematology and serum chemistry analysis. Radiography is performed after terminal exsanguination. Upon gross dissection, major visceral organs are subject to weight analysis.

Following gross dissection, tissues (i.e., liver, spleen, pancreas, stomach, the entire gastrointestinal tract, kidney, reproductive organs, skin and mammary glands, bone, brain, heart, lung, thymus, trachea, esophagus, thyroid, adrenals, urinary bladder, lymph nodes and skeletal muscle) are removed and fixed in 10% buffered Zn-Formalin for histological examination. After fixation, the tissues are processed into paraffin blocks, and 3 mm sections are obtained. All sections are stained with hematoxylin and exosin, and are then subjected to histological analysis.

The spleen, lymph node, and Peyer's patches of both the transgenic and the control mice are subjected to immunohistology analysis with B cell and T cell specific antibodies as follows. The formalin fixed paraffin embedded sections are deparaffinized and hydrated in deionized water. The sections are quenched with 3% hydrogen peroxide, blocked with Protein Block (Lipshaw, Pittsburgh, Pa.), and incubated in rat monoclonal anti-mouse B220 and CD3 (Harlan, Indianapolis, Ind.). Antibody binding is detected by biotinylated rabbit anti-rat immunoglobulins and peroxidase conjugated streptavidin (BioGenex, San Ramon, Calif.) with DAB as a chromagen (BioTek, Santa Barbara, Calif.). Sections are counterstained with hematoxylin.

After necropsy, MLN and sections of spleen and thymus from transgenic animals and control littermates are removed. Single cell suspensions are prepared by gently grinding the tissues with the flat end of a syringe against the bottom of a 100 mm nylon cell strainer (Becton Dickinson, Franklin Lakes, N.J.). Cells are washed twice, counted, and approximately $1 \times 10^6$ cells from each tissue are then incubated for 10 minutes with 0.5 µg CD16/32(FcγIII/II) Fc block in a 20 µL volume. Samples are then stained for 30 minutes at 2–8° C. in a 100 µL volume of PBS (lacking $Ca^+$ and $Mg^+$), 0.1% bovine serum albumin, and 0.01% sodium azide with 0.5 µg antibody of FITC or PE-conjugated monoclonal antibodies against CD90.2 (Thy-1.2), CD45R (B220), CD11b(Mac-1), Gr-1, CD4, or CD8 (PharMingen, San Diego, Calif.). Following antibody binding, the cells are washed and then analyzed by flow cytometry on a FACScan (Becton Dickinson).

While the present invention has been described in terms of the preferred embodiments, it is understood that variations and modifications will occur to those skilled in the art. Therefore, it is intended that the appended claims cover all such equivalent variations that come within the scope of the invention as claimed.

---

What is claimed is:

1. A fusion polypeptide wherein a heterologous amino acid sequence is fused to an amino acid sequence of SEQ ID NO: 7, and wherein the heterologous amino acid sequence is a peptide that:
   a) aids in detection of the fusion polypeptide;
   b) aids in isolation of the fusion polypeptide;
   c) promotes oligomerization of the fusion polypeptide; or
   d) increases stability of the fusion polypeptide.

2. A fusion polypeptide, wherein an amino acid sequence of an IgG constant domain or fragment thereof is fused to an amino acid sequence of SEQ ID NO: 7.

3. A composition comprising the polypeptide of claim 1 or 2 and a pharmaceutically acceptable formulation agent.

4. The composition of claim 3 wherein the pharmaceutically acceptable formulation agent is a carrier, adjuvant, solubilizer, stabilizer, or anti-oxidant.

5. The polypeptide of claim 1 or 2, which is covalently modified with a water-soluble polymer, wherein the water-soluble polymer is polyethylene glycol, monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, or polyvinyl alcohol.

6. The polypeptide of claim 5 wherein the water-soluble polymer is polyethylene glycol or dextran.

* * * * *